(12) United States Patent
Gadelrab et al.

(10) Patent No.: US 11,872,561 B2
(45) Date of Patent: Jan. 16, 2024

(54) SYSTEMS FOR STRETCHING POLYNUCLEOTIDE STRUCTURES

(71) Applicant: Robert Bosch GmbH, Stuttgart (DE)

(72) Inventors: Karim Gadelrab, Boston, MA (US); Mordechai Kornbluth, Brighton, MA (US); Jake Christensen, Elk Grove, CA (US); Christopher Johnson, San Carlos, CA (US); Boris Kozinsky, Waban, MA (US)

(73) Assignee: Robert Bosch GmbH, Stuttgart (DE)

( * ) Notice: Subject to any disclaimer, the term of this patent is extended or adjusted under 35 U.S.C. 154(b) by 372 days.

(21) Appl. No.: 17/200,038

(22) Filed: Mar. 12, 2021

(65) Prior Publication Data

US 2022/0290118 A1      Sep. 15, 2022

(51) Int. Cl.
| | |
|---|---|
| *G01N 33/68* | (2006.01) |
| *G01N 21/33* | (2006.01) |
| *G01N 21/64* | (2006.01) |
| *G01N 33/52* | (2006.01) |
| *C07C 309/65* | (2006.01) |

(Continued)

(52) U.S. Cl.
CPC ....... B01L 3/502761 (2013.01); C12M 35/02 (2013.01); C12N 13/00 (2013.01); C12Q 1/6806 (2013.01); C12Q 1/6837 (2013.01); *B01L 2200/0663* (2013.01); *B01L 2300/0896* (2013.01); *B01L 2400/0415* (2013.01); *G01N 33/48721* (2013.01)

(58) Field of Classification Search
CPC ....... B01L 3/502761; B01L 2200/0663; B01L 2300/0896; B01L 2400/0415; C12M 35/02; C12N 13/00; C12Q 1/6806; C12Q 1/6837; C12Q 1/6869; G01N 33/48721; G01N 27/00
See application file for complete search history.

(56) References Cited

U.S. PATENT DOCUMENTS

| | | | | |
|---|---|---|---|---|
| 6,063,259 A | * | 5/2000 | Wang | G01N 27/3275 204/403.14 |
| 2007/0184446 A1 | * | 8/2007 | Matsumoto | C12Q 1/6837 977/924 |
| 2013/0252235 A1 | | 9/2013 | Tang | |

FOREIGN PATENT DOCUMENTS

| | | |
|---|---|---|
| EP | 2827138 A1 | 1/2015 |
| EP | 3650552 A1 | 5/2020 |
| WO | 2014114665 A1 | 7/2014 |

OTHER PUBLICATIONS

Chan et al., "DNA Mapping Using Microfluidic Stretching and Single-Molecule Detection of Fluorescent Site-Specific Tags", Genome research, 14(6), 10 pages.

(Continued)

*Primary Examiner* — Jennifer Wecker
*Assistant Examiner* — Oyeleye Alexander Alabi
(74) *Attorney, Agent, or Firm* — Brooks Kushman P.C.

(57) ABSTRACT

A system for stretching a polynucleotide structure includes a first electrode configured to generate an electrostatic force perpendicular to a surface of the first electrode and to apply the electrostatic force to the polynucleotide structure to pin an end region of the polynucleotide structure near the surface of the first electrode, and a second electrode configured to generate an electric force along an axial direction of the polynucleotide structure to stretch the polynucleotide structure along the axial direction of the polynucleotide structure into a fully extended form.

20 Claims, 5 Drawing Sheets

(51) Int. Cl.
| | |
|---|---|
| C07C 309/73 | (2006.01) |
| A01N 1/02 | (2006.01) |
| G01N 1/40 | (2006.01) |
| B01L 3/00 | (2006.01) |
| C12M 1/42 | (2006.01) |
| C12N 13/00 | (2006.01) |
| C12Q 1/6806 | (2018.01) |
| C12Q 1/6837 | (2018.01) |
| G01N 33/487 | (2006.01) |

(56) References Cited

OTHER PUBLICATIONS

Douville et al., "DNA linearization through confinement in nanofluidic channels", Anal. Bioanal. Chem. 391, (2008), 15 pages.

Josephs et al., "A Single-Molecule View of Conformational Switching of DNA Tethered to a Gold Electrode", dx.doi.org/10.1021/ja3010946 | J. Am. Chem. Soc. 2012, 134, 10 pages.

Dorfman, K.D., Gupta, D., Jain, A., Muralidhar, A. and Tree, D.R., 2014. Hydrodynamics of DNA confined in nanoslits and nanochannels. The European Physical Journal Special Topics, 223(14), 28 pages.

Maffeo, C., Ngo, T.T., Ha, T. and Aksimentiev, A., 2014. A coarse-grained model of unstructured single-stranded DNA derived from atomistic simulation and single-molecule experiment. Journal of chemical theory and computation, 10(8), pp. 2891-2896.

Wang, C., Bruce, R.L., Duch, E.A., Patel, J.V., Smith, J.T., Astier, Y., Wunsch, B.H., Meshram, S., Galan, A., Scerbo, C. and Pereira, M.A., 2015. Hydrodynamics of diamond-shaped gradient nanopillar arrays for effective DNA translocation into nanochannels. ACS nano, 9(2), pp. 1206-1218.

Levy, S.L. and Craighead, H.G., 2010. DNA manipulation, sorting, and mapping in nanofluidic systems. Chemical Society Reviews, 39(3), pp. 1133-1152.

Zhou, J., Wang, Y., Menard, L.D., Panyukov, S., Rubinstein, M. and Ramsey, J.M., 2017. Enhanced nanochannel translocation and localization of genomic DNA molecules using three-dimensional nanofunnels. Nature communications, 8(1), pp. 1-8.

Ohshima, H., 1999. Electrostatic interaction between a cylinder and a planar surface. Colloid and Polymer Science, 277(6), pp. 563-569.

Dukkipati, V. R. et al., "Precise DNA placement and stretching in electrode gaps using electric fields in a microfluidic system," Applied Physics Letters, vol. 90, No. 083901, Feb. 20, 2007, pp. 083901-1-083901-3, DOI: 10.1063/1.2535556.

Jiang, Y. et al., "Stretching DNA to twice the normal length with single-molecule hydrodynamic trapping," Lab on a Chip, vol. 20, No. 10, Apr. 17, 2020, pp. 1780-1791, DOI: 10.1039/C9LC01028A.

Luan, B. et al., "Controlling the motion of DNA in a nanochannel with transversal alternating electric voltages," Nanotechnology, vol. 25, No. 265101, Jun. 12, 2014, pp. 1-7 DOI: 10.1088/0957-4484/25/26/265101.

Manneschi, C. et al., "Stretching of λ DNA confined in nanochannels with charged walls," Biomicrofluidics, vol. 8, No. 064121, pp. 064121-1-064121-14, Dec. 10, 2014, DOI: 10.1063/1.4904008.

Extended European Search Report for EP 22159635.6, dated Aug. 11, 2022, 13 pages.

\* cited by examiner

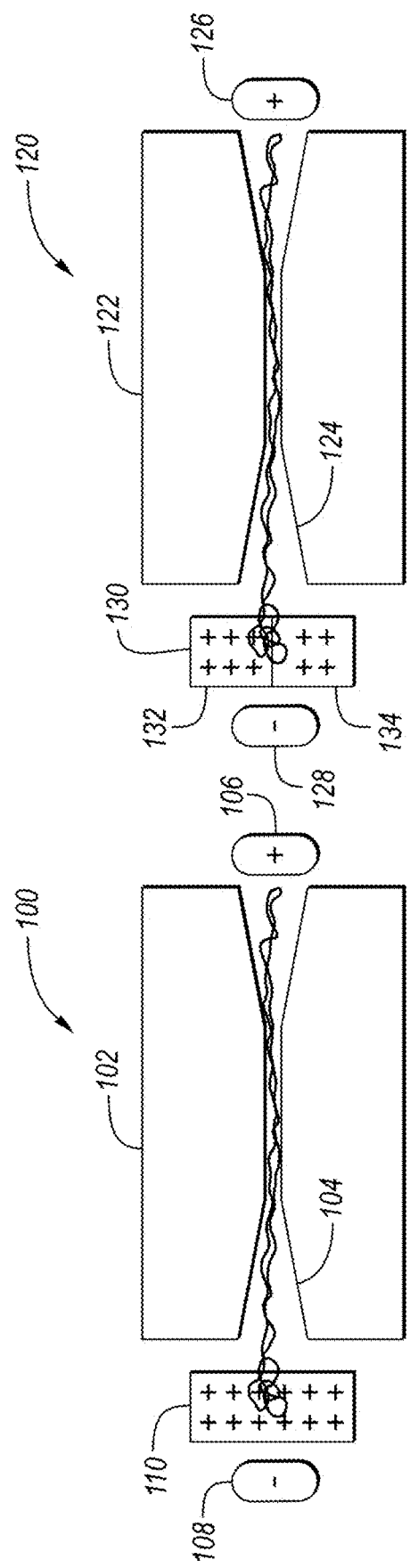

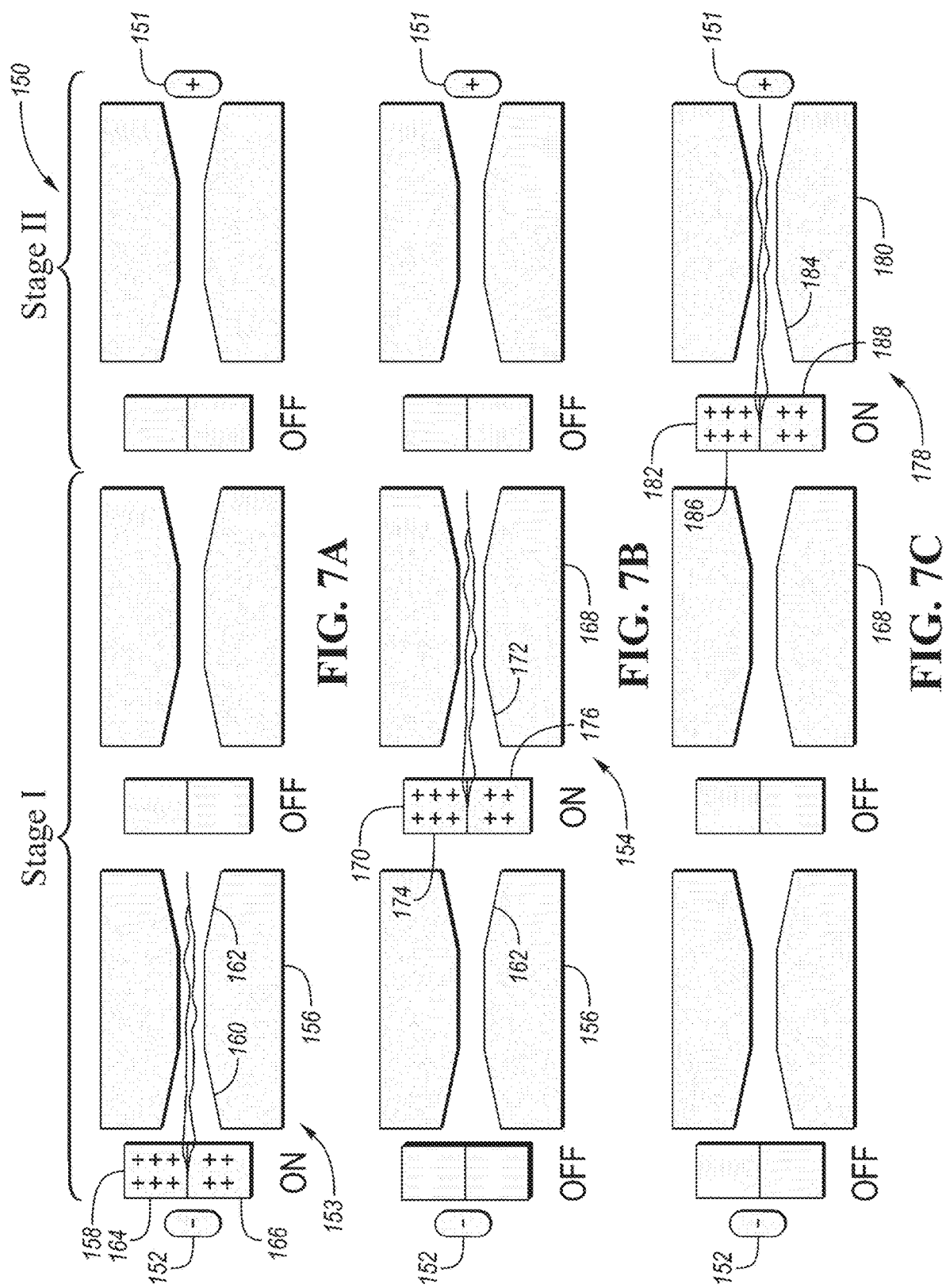

SYSTEMS FOR STRETCHING POLYNUCLEOTIDE STRUCTURES

TECHNICAL FIELD

The present disclosure relates to systems for stretching polynucleotide structures, for example, systems for stretching a deoxyribonucleic acid (DNA) molecule, a ribonucleic acid (RNA) molecule, or a peptide nucleic acid (PNA) molecule.

BACKGROUND

Polynucleotides, such as DNA or RNA, carry digital codes that determine the development of cells in living organisms. Such a fundamental role of polynucleotides drives the vision of achieving personalized medicine and disease treatment. The knowledge of specific gene sequencing and potential harmful mutations may be harnessed to develop personalized drugs. In addition, gene sequencing addresses fundamental biological questions, such as DNA compaction in viral phages, protein interaction in transcribing DNA, and the mechanism of chromatin separation during cell division.

Polynucleotides may undergo major conformational changes through bending and twisting in its natural state, resulting in a highly compacted structure. The natural folded state of polynucleotide complicates the process of accessing the stored genetic information during mapping and sequencing. As such, polynucleotide linearization is essential for analyzing polynucleotide structures and utilizing genetic information for future applications.

SUMMARY

According to one embodiment, a system for stretching a polynucleotide structure is disclosed. The polynucleotide structure may be a DNA structure, an RNA structure, or a PNA structure. The DNA structure may be a DNA molecule or a single-stranded DNA. The system may include a first electrode configured to generate an electrostatic force perpendicular to a surface of the first electrode and to apply the electrostatic force to the polynucleotide structure to pin an end region of the polynucleotide structure near the surface of the first electrode. The system may also include a second electrode configured to generate an electric force along an axial direction of the polynucleotide structure to stretch the polynucleotide structure along the axial direction of the polynucleotide structure into a fully extended form.

According to another embodiment, a system for stretching a polynucleotide structure is disclosed. The system may include a nanochannel having an inlet, an outlet, a first end region, and a second end region. The system may further include a first electrode positioned adjacent to a first end region of the nanochannel. The first electrode may be positively charged. The system may also include a second electrode positioned adjacent to a second end region of the nanochannel. The second electrode may be negatively charged. The first and second electrodes may be configured to generate an electric force along an axial direction of the nanochannel to guide the polynucleotide structure into the nanochannel to stretch the polynucleotide structure along the axial direction of the nanochannel. The system may further include a third electrode positioned adjacent to the inlet of the nanochannel and configured to generate an electrostatic force perpendicular to a surface of the third electrode and to apply the electrostatic force to the polynucleotide structure to pin an end region of the polynucleotide structure near the surface of the third electrode.

According to yet another embodiment, a multi-stage system for stretching a polynucleotide structure is disclosed. The system may include a first electrode positioned at a first end region of the multi-stage system. The first electrode may be positively charged. The system may further include a second electrode positioned at a second end region of the multi-stage system. The second electrode may be negatively charged. The first and second electrode may be aligned axially. The system may also include a first nanochannel having a first inlet and a first outlet. The system may further include a third electrode positioned adjacent to the first inlet of the first nanochannel and configured to sense a presence of the polynucleotide structure and to generate a first electrostatic force perpendicular to a surface of the third electrode and to apply the first electrostatic force to the polynucleotide structure to pin a first end region of the polynucleotide structure near the surface of the third electrode. The first and second electrodes may be configured to generate a first electric force to guide the polynucleotide structure through the first nanochannel. The system may also include a second nanochannel having a second inlet and a second outlet. The second nanochannel being positioned adjacent to the first outlet of the first nanochannel. The system may further include a fourth electrode positioned adjacent to the second inlet of the second nanochannel and between the first and the second nanochannel. The fourth electrode may be configured to sense the presence of a second end region of the polynucleotide structure when a portion of the polynucleotide structure extends beyond the first outlet of the first nanochannel and to generate a second electrostatic force perpendicular to a surface of the third electrode. The fourth electrode may be activated upon sensing the presence of the second end region of the polynucleotide structure. The third electrode may be deactivated to release the first end region of the polynucleotide structure. The fourth electrode may be configured to apply the second electrostatic force to the polynucleotide structure to pin the second end region of the polynucleotide structure near the surface of the fourth electrode. The first and second electrodes being configured to generate a second electric force to guide the polynucleotide structure through the second nanochannel. The system may further include a third nanochannel having a third inlet and a third outlet. The third nanochannel may be positioned adjacent to the second outlet of the second nanochannel. The system may also include a fifth electrode positioned adjacent to the third inlet of the third nanochannel and between the second and the third nanochannel. The fifth electrode may be configured to sense a presence of the first end region of the polynucleotide structure when a portion of the polynucleotide structure extends beyond the second outlet of the second nanochannel and to generate a third electrostatic force perpendicular to a surface of the fifth electrode. The fifth electrode may be activated upon sensing the presence of the first end region of the polynucleotide structure. The third electrode may be deactivated to release the second end region of the polynucleotide structure. The fifth electrode may be configured to apply the third electrostatic force to the polynucleotide structure to pin the first end region of the polynucleotide structure near the surface of the fifth electrode. The first and second electrodes may be configured to generate a third electric force to guide the polynucleotide structure through the third nanochannel.

BRIEF DESCRIPTION OF THE DRAWINGS

FIG. 5 depicts a schematic, perspective top view of a second embodiment of the present disclosure.

FIG. 6 depicts a schematic, perspective top view of a third embodiment of the present disclosure.

FIGS. 7A, 7B and 7C depict a schematic, perspective top view of a system configured to perform a multi-stage polynucleotide stretching process for polynucleotide sensing or sequencing purposes.

DETAILED DESCRIPTION

Figure 1:
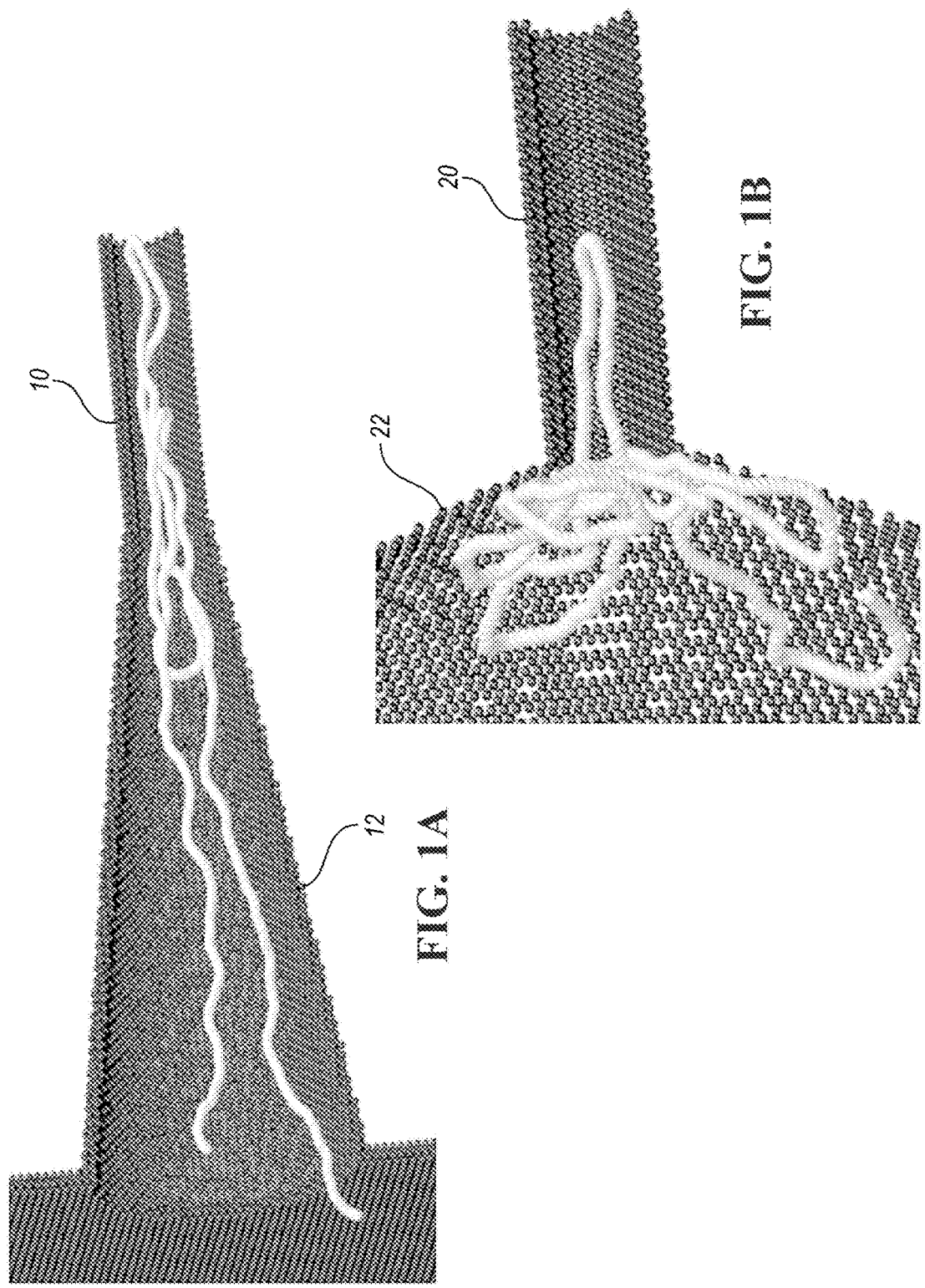
FIG. 1A depicts a schematic diagram of a molecular dynamics simulation of a process in which a DNA molecule is driven into a first nanochannel under the influence of an electric force applied along an axial direction of the first nanochannel.
FIG. 1B depicts a schematic diagram of a molecular dynamics simulation of a process in which the same DNA molecule as described in FIG. 1A is driven into a second nanochannel under the influence of the same electric force as that in FIG. 1A.

Embodiments of the present disclosure are described herein. It is to be understood, however, that the disclosed embodiments are merely examples and other embodiments can take various and alternative forms. The figures are not necessarily to scale; some features could be exaggerated or minimized to show details of components. Therefore, specific structural and functional details disclosed herein are not to be interpreted as limiting, but merely as a representative basis for teaching one skilled in the art to variously employ the embodiments. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for applications or implementations.

This present disclosure is not limited to the specific embodiments and methods described below, as specific components and/or conditions may, of course, vary. Furthermore, the terminology used herein is used only for the purpose of describing embodiments of the present disclosure and is not intended to be limiting in any way.

As used in the specification and the appended claims, the singular form "a," "an," and "the" comprise plural referents unless the context clearly indicates otherwise. For example, reference to a component in the singular is intended to comprise a plurality of components.

The description of a group or class of materials as suitable for a given purpose in connection with one or more embodiments implies that mixtures of any two or more of the members of the group or class are suitable. Description of constituents in chemical terms refers to the constituents at the time of addition to any combination specified in the description and does not necessarily preclude chemical interactions among constituents of the mixture once mixed.

Except where expressly indicated, all numerical quantities in this description indicating dimensions or material properties are to be understood as modified by the word "about" in describing the broadest scope of the present disclosure.

The first definition of an acronym or other abbreviation applies to all subsequent uses herein of the same abbreviation and applies mutatis mutandis to normal grammatical variations of the initially defined abbreviation. Unless expressly stated to the contrary, measurement of a property is determined by the same technique as previously or later referenced for the same property.

The term "substantially" may be used herein to describe disclosed or claimed embodiments. The term "substantially" may modify any value or relative characteristic disclosed or claimed in the present disclosure. "Substantially" may signify that the value or relative characteristic it modifies is within ±0%, 0.1%, 0.5%, 1%, 2%, 3%, 4%, 5% or 10% of the value or relative characteristic.

Reference is being made in detail to compositions, embodiments, and methods of embodiments known to the inventors. However, disclosed embodiments are merely exemplary of the present disclosure which may be embodied in various and alternative forms. Therefore, specific details disclosed herein are not to be interpreted as limiting, rather merely as representative bases for teaching one skilled in the art to variously employ the present disclosure.

Various linearization techniques have been proposed to stretch a polynucleotide structure, such as those using hydrodynamic forces, optical tweezers, or nano-confinement. For example, nanochannels, when designed to the proper size and/or shape, may provide a viable tool to maintain an extended DNA structure. Generally, there are two stages to shuttle a DNA structure, such as a DNA molecule or a single-strand DNA, into a nanochannel: first, the DNA structure is driven to an inlet of the nanochannel from a reservoir through drift or diffusion; and second, the DNA structure is shuttled inside the nanochannel under the influence of an external force, such as a hydrodynamic or electrostatic force. With the help of the external force, the DNA structure can overcome the entropic barrier of uncoiling and transform into an extended form.

Carefully designed topological features at the inlet of the nanochannel may significantly reduce the external force required to shuttle the DNA structure into the nanochannel. For example, introducing a multiscale array of pillars before the inlet of the nanochannel may cause the DNA structure to untangle and undergo reptation motion between the pillars. However, the applicability of such an approach to unfold DNA is limited by the requirement of a small gap between the pillars and the inlet of the nanochannel. Such a small gap may adversely lead the untangled DNA structure to recoil. For another example, to achieve DNA linearization, the nanochannel may have an inlet that is in a conical shape to allow a DNA structure to gradually extend at the inlet while under the influence of a lateral force applied along an axis direction of the nanochannel. However, the DNA structure, in such a setting of the nanochannel, may not be fully extended before entering the nanochannel. Further, controlling a shuttling speed of the DNA structure is also a challenge to be overcome. Therefore, there is a need to unfold a DNA structure as well as other polynucleotide structures (e.g. RNAs or PNAs) in a more effective manner.

Aspects of the present disclose relate to systems for stretching a polynucleotide structure. The polynucleotide structure may be a DNA structure, an RNA structure, or a PNA structure. The DNA structure may be a DNA molecule or a single-stranded DNA. In one embodiment, aspects of the present disclosure are directed to a system that has a first electrode configured to generate an electrostatic force to pin an end region of the polynucleotide structure near the surface of the first electrode, and that on the other hand, has a second electrode configured to generate an electric force along an axial direction of the polynucleotide structure to stretch the polynucleotide structure along the axial direction of the polynucleotide structure into a fully extended form. In another embodiment, aspects of the present disclosure are directed to a system that has a nanochannel having an inlet and an outlet, a first electrode positioned adjacent to the inlet of the nanochannel and configured to generate an electrostatic force perpendicular to pin an end region of the polynucleotide structure near the surface of the first electrode, and that on the other hand, has a second electrode positioned inside the nanochannel and configured to generate an electric force along an axial direction of the nanochannel to guide the polynucleotide structure into the nanochannel to stretch the polynucleotide structure along the axial direction of the nanochannel. In yet another embodiment, aspects of the present disclosure are directed to a multi-stage system that includes a pre-sensing stage and a sensing stage, where a polynucleotide structure is fully extended during the pre-sensing stage before entering the sensing stage for effective sensing or sequencing purposes.

FIG. 1A depicts a schematic diagram of a molecular dynamics simulation of a process in which a DNA molecule is driven into a first nanochannel 10 under the influence of an electric force applied along an axial direction of the first nanochannel 10. The DNA molecule may include 2,500 base pairs. The first nanochannel 10 may have an inlet 12 with a 10-degree tapered configuration. The electric force may be an electric field. The electric field may be around $10^3$ V/cm.

FIG. 1B depicts a schematic diagram of a molecular dynamics simulation of a process in which the same DNA molecule as described in FIG. 1A is driven into a second nanochannel 20 under the influence of the same electric force as that in FIG. 1A. The electric force is also applied along an axial direction of the second nanochannel 20. Unlike the first nanochannel 10, the second nanochannel 20 has an inlet 22 with a 70-degree tapered configuration.

In both FIGS. 1A and 1B, the DNA molecule may first be driven to a region near the inlet of each nanochannel through drift or diffusion under the influence of the electric field applied along the axial direction of each nanochannel. Referring to FIG. 1A, as the DNA molecule advances toward the inlet 12 of the first nanochannel 10, the gradual increase in the two-dimensional (2D) confinement of the inlet 12 compresses the DNA molecule and force the DNA molecule to transform into an extended form such that the DNA molecule can be shuttled inside the first nanochannel 10. On the other hand, in FIG. 1B, due to the steep angle of the inlet 22 of the second nanochannel 20, the DNA molecule, while under the influence of the same electric force as that in FIG. 1A, may entangle at the inlet 22 but rather transform into an extended form. The entangled form of the DNA molecule may slow down the process of shuttling the DNA molecule into the second nanochannel 20. To unfold the entangled form of the DNA molecule and to shuttle it inside the second nanochannel 20, a stronger electric force, i.e. more energy, may thus be required to help guide the DNA molecule into the second nanochannel 20.

In view of FIGS. 1A and 1B, the structural configuration of the inlet of a nanochannel appears to have a significant impact on DNA stretching. In general, an inlet that has a relatively small-degree tapered structure may allow a more effective DNA stretching, whereas an inlet that has a relatively large-degree tapered structure may impede the process of DNA stretching.

Apart from the impact from the tapered structure of the inlet of a nanochannel, molecular dynamics simulations further indicate that a DNA structure, such as a DNA molecule or a single-stranded DNA, may enter the nanochannel in a hairpin style, that is, the DNA structure enters the nanochannel with free end regions of the DNA structure being buried in a middle region of the DNA. This is expected because, under the influence of the electric force applied to the axial direction of the nanochannel, it may be easier for the middle region of the DNA structure to enter the nanochannel than for the free end regions to do so. Such a phenomenon may be more obvious as the length or the mass of the DNA structure increases. Therefore, simply relying on the electric force to guide the DNA structure into the nanochannel may not allow the DNA structure to be fully extended for sensing or sequencing purposes.

Figure 2:
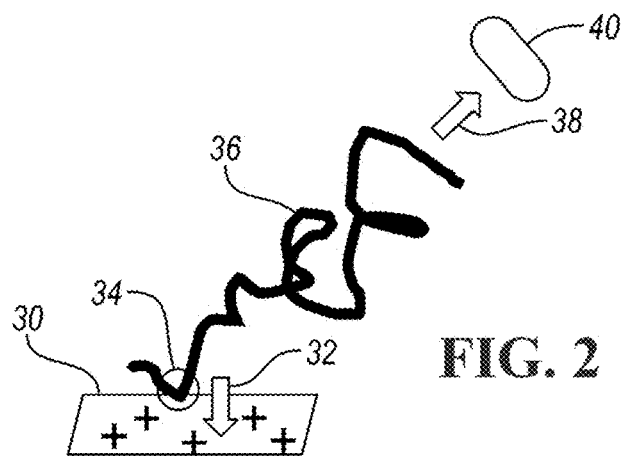
FIG. 2 depicts a schematic diagram of a first embodiment of the present disclosure.

FIG. 2 depicts a schematic diagram of a first embodiment of the present disclosure. As shown in FIG. 2, to stretch a polynucleotide structure 36, an electrically charged electrode 30 (e.g. a first electrode) may provide an electrostatic force 32 to pin an end region 34 of the polynucleotide structure 36 near a surface of the first electrode 30; and on the other hand, an electric force 38 may be provided, e.g. by a second electrode 40, along an axial direction of the polynucleotide structure 36 to stretch the polynucleotide structure 36 along the axial direction thereof. The shape, size and position of the second electrode 40, as indicated in FIG. 2, are only exemplary. The polynucleotide structure 36 may be a DNA structure, an RNA structure, or a PNA structure. The DNA structure may be a DNA molecule or single-stranded DNA. The electric force 38 may be an electric field generated by the second electrode 40. As depicted in FIG. 2, the first electrode 30 is positively charged, and the electrostatic force 32 applied to the polynucleotide structure 36 is perpendicular to the surface of the first electrode 30. Under the influence of the dual forces 32 and 38, the polynucleotide structure 36 is subject to non-uniform forces along the polynucleotide structure, allowing the polynucleotide structure to be fully extended.

The amount of the electrostatic force 32 applied to the polynucleotide structure 36 by the first electrode 30 may depend on factors such as a surface electrical potential (i.e. the amount of charge) of the first electrode 30 or the distance between the polynucleotide structure 36 and the surface of the first electrode 30. For example, a stronger electrostatic force 32 may be generated by the first electrode 30 when the surface electrical potential of the first electrode 30 is relatively high. For another example, when the polynucleotide structure 36 is not near the surface of the first electrode 30, the electrostatic force 32 applied to the polynucleotide structure 36 may be weak or none. In some embodiments, the width of the first electrode 30 may be 100 nm.

Similarly, the amount of the electric force 38 applied along the axial direction of the polynucleotide structure 36 may depend on factors such as the strength of the electric field generated by the second electrode 40 or the size of the polynucleotide structure 36. In any event, to enable the polynucleotide structure 36 to unfold under the influence of the dual forces, the amount of the electric force 38 is great enough to stretch the polynucleotide structure 36 along the axial direction of the polynucleotide structure 36 while ensuring that the end region 34 of the polynucleotide structure 36 remains electrostatically pinned near the surface of the first electrode 30.

Figure 3A:
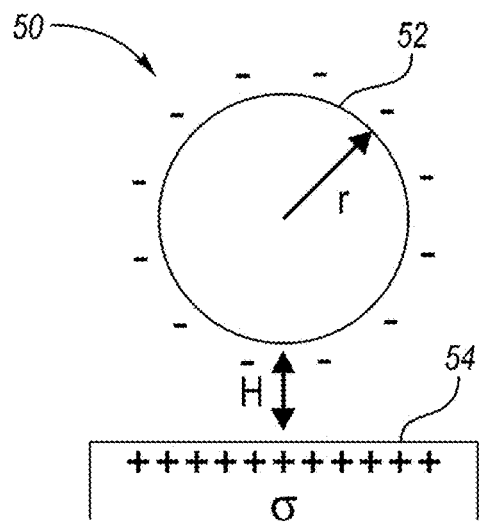
FIG. 3A depicts a schematic diagram illustrating a model of a cylinder half-plane system.

FIG. 3A depicts a schematic diagram illustrating a model of a cylinder half-plane system. The system 50 may be used to evaluate the interaction between a DNA structure and an electrode. The DNA structure may be a DNA molecule or single-stranded DNA. The cylinder 52 represents the DNA structure. The cylinder 52 has a diameter of 4 nm (i.e. the radius, r, is 2 nm) which mimics the actual diameter of the DNA structure in a fluid. As shown in FIG. 3A, the cylinder 52 is negatively charged with a linear charge density of −0.3 $C/m^2$ in a 0.5 M electrolyte. The half plane 54 represents the electrode, the surface of which, as shown in FIG. 3A, is positively charged.

Figure 3B:
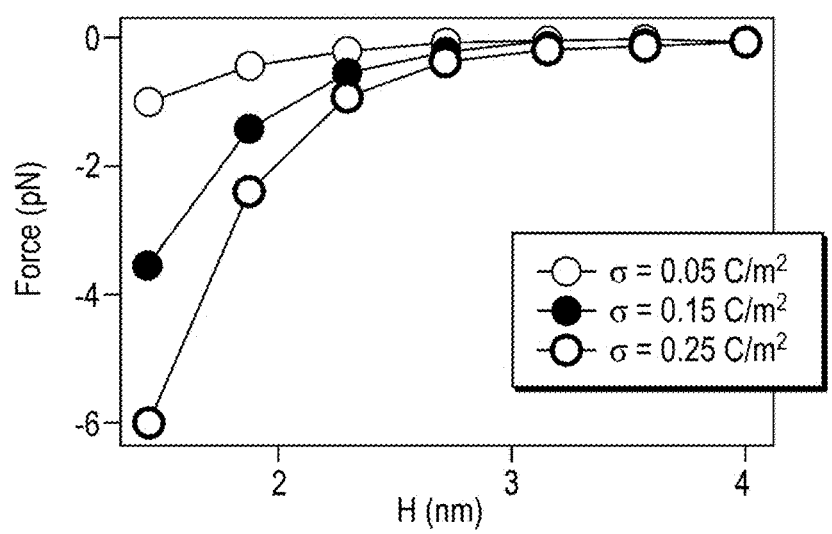
FIG. 3B depicts a schematic diagram showing an amount of the electrostatic force applied to the cylinder by the positively charged half plane as a function of a distance between the cylinder and the half plane.

FIG. 3B depicts a schematic diagram showing an amount of the electrostatic force (pN) applied to the cylinder 52 by the positively charged half plane 54 as a function of a distance (H, nm) between the cylinder 52 and the half plane 54. The value of the electrostatic force may represent a distributed force applied to per nucleotide in the DNA structure. A total force applied to the DNA structure may then be calculated based on the distributed force per nucleotide and a size of the DNA structure. FIG. 3B illustrates three scenarios where the surface of the half plane 54 is charged with different amounts of positive charges, 0.05 $C/m^2$, 0.15 $C/m^2$, or 0.25 $C/m^2$, respectively. Referring to FIG. 3B, the electrostatic force applied to the cylinder 52 may increase as the amount of the positive charge on the surface of the half plane 54 also increases. In addition, as shown in FIG. 3B, as the distance between the cylinder 52 and the half plane 54 increases, the electrostatic force applied to the cylinder 52 may decrease. The electrostatic force appears to be close to zero when the distance between the cylinder 52 and the half plane 54 is over 3 nm. This indicates that when applying an electrostatic force onto a DNA structure, the DNA structure may be pinned within a distance less than 3 nm from the surface of a charged electrode.

Figure 4A:
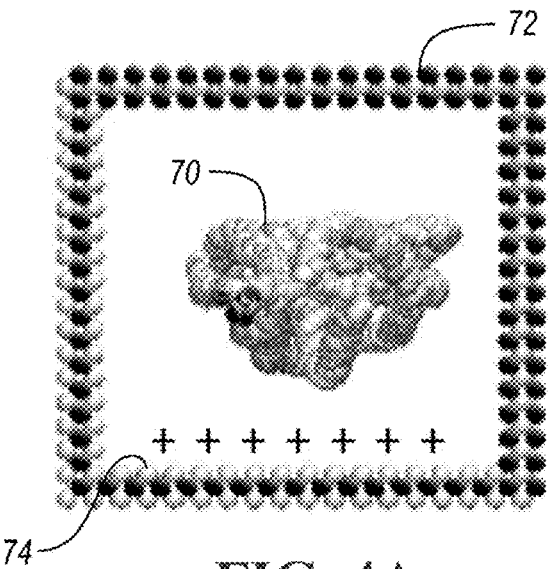
FIG. 4A depicts a schematic diagram showing a molecular dynamics simulation of a DNA structure confined inside a nanochannel.

FIG. 4A depicts a schematic diagram showing a molecular dynamics simulation of a DNA structure confined inside a nanochannel. The DNA structure may be a DNA molecule or single-stranded DNA. FIG. 4A shows a perspective view of the structure 70 along an axial direction of the nanochannel 72. The bottom surface 74 of the nanochannel 72 is positively charged. The diameter of the nanochannel 72 is around 20 nm. In FIG. 4A, no electric force is applied along the axial direction of the nanochannel 72 (i.e. nor electric force is applied along an axial direction of the DNA structure 70). As depicted, the DNA structure 70 may fluctuate within the nanochannel 72.

Figure 4B:
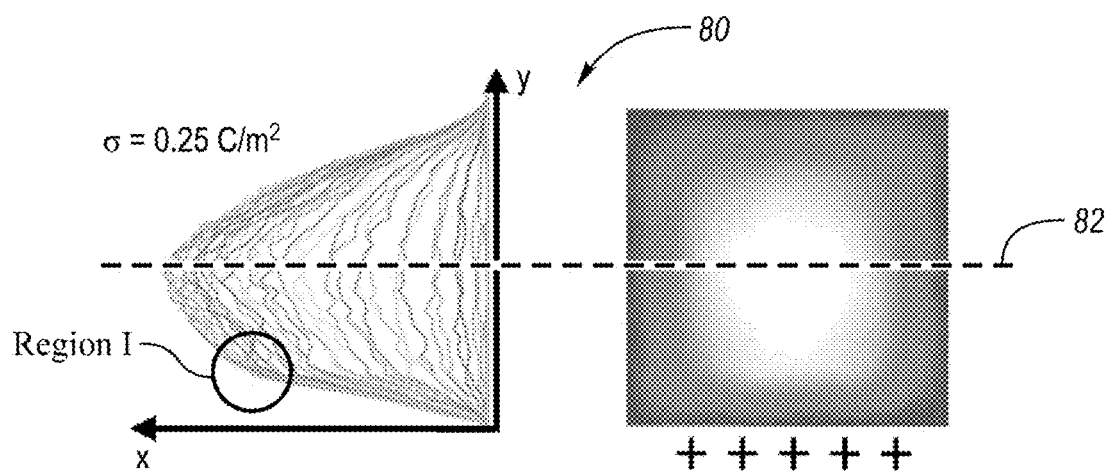
FIG. 4B depicts a first density map showing locations of nucleotides of the DNA structure as described in FIG. 4A.

FIG. 4B depicts a first density map showing locations of nucleotides of the DNA structure as described in FIG. 4A. The first density map 80 represents the scenario where a surface charge density of the bottom surface 74 of the nanochannel 72 is 0.25 $C/m^2$. The x axis represents a density of the nucleotides in the DNA structure along the axial direction of the nanochannel 72. The y axis represents a height direction of the nanochannel 72. As shown in FIG. 4B, under the influence of the electrostatic force applied by the positively charged bottom surface 74 of the nanochannel 72, the first density map 80 exhibits an asymmetry of the locations of the nucleotides in the DNA structure 70. Particularly, the nucleotides in region I appear to deviate more from the center of the nanochannel 72 and be closer to the bottom surface 74 of the nanochannel 72. However, despite the asymmetry of the nucleotide distribution, the DNA structure 70, in general, still appears to be positioned near the center of the nanochannel 72, as indicated by the dotted line 82 showing the highest peak appeared near the center of the nanochannel 72.

Figure 4C:
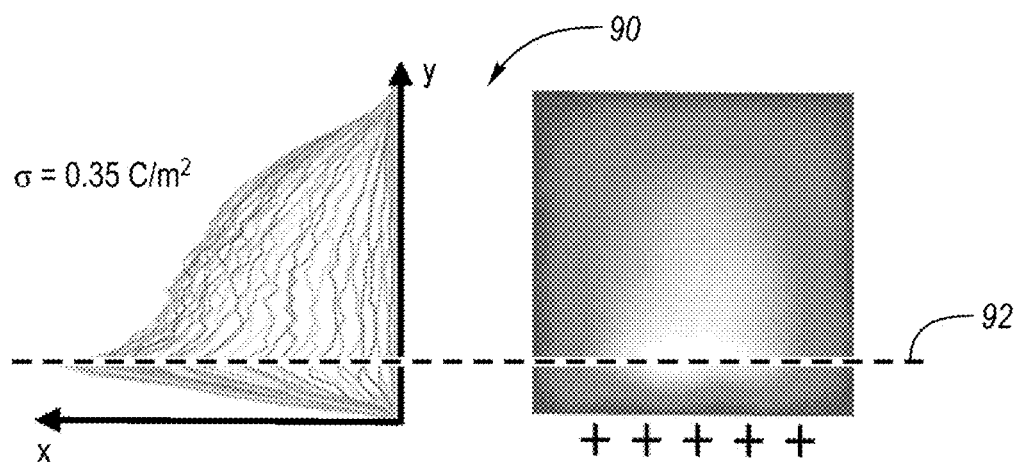
FIG. 4C depicts a second density map showing locations of nucleotides of the DNA structure as described in FIG. 4A.

FIG. 4C depicts a second density map showing locations of nucleotides of the DNA structure as described in FIG. 4A. The second density map 90 represents the scenario where a surface charge density of the bottom surface 74 of the nanochannel 72 is 0.35 $C/m^2$. The x axis represents a density of the nucleotides in the DNA structure along the axial direction of the nanochannel 72. The y axis represents a height direction of the nanochannel 72. As discussed in FIGS. 3A and 3B, when the amount of charge on a surface of an electrode is high, the electrostatic force applied to a nearby DNA structure may increase. Accordingly, as shown in FIG. 4C, although the second density map 90 displays an asymmetry of the locations of nucleotides in the DNA structure 70, the nucleotides appear to be much closer to the bottom surface 74 of the nanochannel 72 when compared to those in FIG. 4B, as indicated by the dotted line 92 showing the highest peak near the bottom surface 74 of the nanochannel 72.

In view of FIGS. 4A, 4B and 4C, these data may suggest that when an end region of a polynucleotide structure is electrostatically pinned near a surface of a charged electrode, the remaining part of the polynucleotide structure may travel across a nanochannel under the influence of an electric force (e.g. an electric field) applied along an axial direction of the nanochannel.

FIG. 5 depicts a schematic, perspective top view of a second embodiment of the present disclosure. FIG. 5 shows a single setup 100 configured to stretch a polynucleotide structure along an axial direction of a nanochannel 102. The polynucleotide structure may be a DNA structure, an RNA structure, or a PNA structure. The DNA structure may be a DNA molecule or single-stranded DNA. As shown in FIG. 5, the single setup 100 may include a nanochannel 102 with a tapered inlet 104. The nanochannel 102 may further include a first electrode 106 and a second electrode 108. The first electrode 106 may be positively charged. The second electrode 108 may be negatively charged. The first and second electrodes 106 and 108 can apply an electric force along an axial direction of the nanochannel 102. The electric force may be an electric field. The shape, size, and position of the first and second electrodes 106 and 108, as depicted in FIG. 5, are exemplary. In some embodiments, the first and second electrodes 106 and 108 may be positioned adjacent to end regions of the nanochannel 102, respectively. The end regions of the nanochannel 102 may be external to the nanochannel 102. The single setup 100 may also include a third electrode 110 situated adjacent to the inlet 104 of the nanochannel 102. The surface of the third electrode 110 may be positively charged such that it can apply an electrostatic force to pin the polynucleotide structure near the surface thereof.

Referring to FIG. 5, after a polynucleotide structure is driven to a region near the inlet 104 of the nanochannel 102, the electrically charged third electrode 110 may generate an electrostatic force perpendicular to the surface thereof. The electrostatic force may pin an end region of the polynucleotide structure near the surface of the third electrode 110. As discussed in FIGS. 3A and 3B, the end region of the polynucleotide structure may be within a distance less than 3 nm from the surface of the third electrode 110. On the other hand, the first and second electrodes 106 and 108 may apply an electric force to the remaining part of the polynucleotide structure along the axial direction of the nanochannel 102 to unfold the polynucleotide structure. As such, under the influence of the dual forces, the polynucleotide structure is subject to non-uniform forces along an axis of the polynucleotide structure, allowing the polynucleotide structure to be fully extended.

The length of the nanochannel 102 is configured such that a portion of the polynucleotide structure in a fully extended form extends beyond the outlet of the nanochannel 102. In some embodiments, the length of the nanochannel 102 is half of the length of a fully extended polynucleotide. The nanochannel 102 may include a tapered inlet 104 with a taper angle less than 45 degree. The width of the third electrode 110 may be 100 nm. The amount of the electrostatic force applied to the polynucleotide structure by the third electrode 110 may depend on factors such as a surface electrical potential (i.e. the amount of charge) of the third electrode 110 or the distance between the polynucleotide structure and the surface of the third electrode 110. The amount of the electric force applied to the axial direction of the nanochannel 102 may depend on factors such as the strength of the electric field generated by the first and second electrodes 106 and 108 or the size of the polynucleotide structure. In any event, to enable the polynucleotide structure to unfold under the influence of the dual forces, the amount of the electric force is great enough to stretch the polynucleotide structure along the axial direction of the nanochannel 102 while ensuring that the end region of the polynucleotide structure remains electrostatically pinned near the surface of the third electrode 110.

FIG. 6 depicts a schematic, perspective top view of a third embodiment of the present disclosure. FIG. 6 shows another single setup 120 configured to stretch a polynucleotide structure along an axial direction of a nanochannel 122. The polynucleotide structure may be a DNA structure, an RNA structure, or a PNA structure. The DNA structure may be a DNA molecule or single-stranded DNA. As shown in FIG. 6, the single setup 120 may include a nanochannel 122 with a tapered inlet 124. The nanochannel 122 may further include a first electrode 126 and a second electrode 128. The first electrode 126 may be positively charged. The second electrode 128 may be negatively charged. The first and second electrodes 126 and 128 can apply an electric force along the axial direction of the nanochannel 122. The electric force may be an electric field. The shape, size, and position of the first and second electrodes 126 and 128, as depicted in FIG. 6, are exemplary. In some embodiments, the first and second electrodes 126 and 128 may be positioned adjacent to end regions of the nanochannel 122, respectively. The end regions of the nanochannel 122 may be external to the nanochannel 122. The single setup 120 may also include a third electrode 130 situated adjacent to the inlet 124 of the nanochannel 122.

In this embodiment, the third electrode 130 may further be divided into a first half 132 and a second half 134, where each half of the third electrode 130 may be positively charged with different amount of positive charges. As such, the two halves of the third electrode 130 possess different surface electrical potentials. Due to the difference in the surface electrical potentials, the third electrode 130 may sense the presence of a nearby polynucleotide structure. Systems and methods of sensing the presence of a polynucleotide structure, such as a DNA molecule or single-stranded DNA, using an electrode that can provide an electrostatic force to pin the polynucleotide structure near a surface of the electrode have been disclosed in U.S. patent application Ser. No. 16/009,766, which is hereby incorporated by reference in its entirety. Generally, due to the difference in the surface electrical potentials of the two halves of the third electrode 130, tunneling junctions may exist between the two halves, 132 and 134. When a polynucleotide structure is driven to a region near the surface of the third electrode 130 (i.e. also near the inlet 124 of the nanochannel 120), electrons may tunnel between the two halves of the third electrode 130, thereby generating a current. A controller (not shown) operatively connected to the third electrode 130 may then sense the current and determine that a polynucleotide structure is near the surface of the third electrode 130. Thereafter, the controller may order the third electrode 130 to ramp up the surface electrical potentials to pin the polynucleotide structure near the surface thereof.

The length of the nanochannel 120 is configured such that a portion of the polynucleotide structure in a fully extended form extends beyond the outlet of the nanochannel 120. In some embodiments, the length of the nanochannel 120 is half of the length of a fully extended polynucleotide. The nanochannel 120 may include a tapered inlet 124 with a taper angle less than 45 degree. The width of the third electrode 130 may be 100 nm. The amount of the electrostatic force applied to the polynucleotide structure by the third electrode 130 may depend on factors such as a surface electrical potential (i.e. the amount of charge) of the third electrode 130 or the distance between the polynucleotide structure and the surface of the third electrode 130. The amount of the electric force applied to the axial direction of the nanochannel 120 may depend on factors such as the strength of the electric field generated by the first and second electrodes 126 and 128 or the size of the polynucleotide structure. In any event, to enable the polynucleotide structure to unfold under the influence of the two forces, the amount of the electric force is great enough to stretch the polynucleotide structure along the axial direction of the nanochannel 120 while ensuring that the end region of the polynucleotide structure remains electrostatically pinned near the surface of the third electrode 130.

In view of FIGS. 5 and 6, by incorporating an electrode adjacent to an inlet of a nanochannel to pin a polynucleotide structure near a surface thereof and by simultaneously applying an electric force (e.g. an electric field) along an axial direction of the nanochannel, the polynucleotide structure may be extended along the axial direction of the nanochannel. However, due to the complexity of polynucleotide structures, subjecting the polynucleotide structure to the dual forces one time may not fully unfold the polynucleotide structure for sensing or sequencing purposes. Therefore, to achieve a more effective polynucleotide sensing or sequencing purpose, more than one time of such a stretching process may be advised in one or more embodiments.

FIG. 7 depicts a schematic, perspective top view of a system configured to perform a multi-stage polynucleotide stretching process for polynucleotide sensing or sequencing purposes. In general, the system 150 may include two stages: a pre-sensing stage (Stage I) and a sensing stage (Stage II). The system 150 may further include a first electrode 151 and a second electrode 152. The first electrode 151 may be positively charged and positioned adjacent to an end region of the system 150. The second electrode 152 may be negatively charged and positioned adjacent to the other end region of the system 150. The first and second electrodes 151 and 152 can apply an electric force along an axial direction of the system 150. The electric force may be an electric field. The shape, size, and position of the first and second electrodes 151 and 152, as depicted in FIG. 7, are exemplary.

During the pre-sensing stage, a polynucleotide structure, such as a DNA structure, an RNA structure, or a PNA structure, may be fully extended under the dual influences of an electrostatic force and an electric force (e.g. an electric field), as described in FIG. 6. In order to fully extend the polynucleotide structure before the sensing stage, at least two of the single setups as illustrated in FIG. 6 may be used. FIG. 7 shows the usage of two single setups. In some other embodiments, more than two of such single setups may be used to fully extend a polynucleotide structure.

Referring to FIGS. 7A and 7B, the pre-sensing stage includes a first single setup 153 and a second single setup 154. The first single setup 153 further includes a first nanochannel 156 and a third electrode 158 positioned adjacent to an inlet 160 of the first nanochannel 156. The first nanochannel 156 may also include an outlet 162. The third electrode 158 may further be divided into a first half 164 and a second half 166, where each half of the third electrode 158 may be positively charged with different amount of positive charges. As discussed in FIG. 6, due to the difference in the surface electrical potentials, the third electrode 158 may sense the presence of a nearby polynucleotide structure. Upon sensing the presence of a polynucleotide structure, the third electrode 158 may apply a first electrostatic force toward the polynucleotide structure to pin a first end region of the polynucleotide structure near a surface thereof, while, at the same time, a first electric force may be generated by the first and second electrodes 151 and 152 of the system 150 and applied along an axial direction of the first nanochannel 156 to unfold the remaining part of the polynucleotide structure. The axial direction of the first nanochannel 156 may be aligned with the axial direction of the system 150.

Further, referring to FIG. 7B, the second single setup 154 includes a second nanochannel 168 and a fourth electrode 170 positioned between the outlet 162 of the first nanochannel 156 and an inlet 172 of the second nanochannel 168. The fourth electrode 170 may also be divided into a first half 174 and a second half 176, where each half of the fourth electrode 170 may be positively charged with different amount of positive charges. As such, the fourth electrode 170 may also sense the presence of a nearby polynucleotide structure. The first and second single setups, 153 and 154, may be aligned in such a manner that when a portion of the polynucleotide structure extends beyond the first outlet 162 of the first nanochannel 156, a second end region of the polynucleotide structure may be sensed by the fourth electrode 170 of the second single setup 154. Upon the fourth electrode 170 of the second single setup 154 senses the second end region of the polynucleotide structure, the fourth electrode 170 may be activated (i.e. ON) to generate a second electrostatic force, and at the same time, the third electrode 158 of the first single setup 152 may be deactivated (i.e. OFF). The deactivation of the third electrode 158 may cause the third electrode 158 to release the first end region of the polynucleotide structure. At this time, the fourth electrode 170 may apply the second electrostatic force to the second end region of the polynucleotide structure to pin the second end region of the polynucleotide structure near a surface thereof. On the other hand, the remaining part of the polynucleotide structure may be subject to a second electric force applied along an axial direction of the second nanochannel 168 by the first and second electrodes 151 and 152 of the system 150 to be unfolded along the axial direction of the second nanochannel 168. The axial direction of the second nanochannel 168 may be aligned with the axial direction of the system 150.

As such, after the polynucleotide structure has gone through the stretching process provided by the first and second single setups, 153 and 154, in the pre-sensing stage, the polynucleotide structure is expected to be in a fully extended form suitable for polynucleotide sensing or sequencing.

Now referring to FIG. 7C, the sensing stage includes a third single setup 178. The third single setup 178 further includes a third nanochannel 180 for polynucleotide sensing or sequencing purposes, and a fifth electrode 182 positioned adjacent to an inlet 184 of the third nanochannel 180. The fifth electrode 182 may also be divided into a first half 186 and a second half 188, where each half of the fifth electrode 182 may be positively charged with different amount of positive charges. As such, the fifth electrode 182 may also sense the presence of a nearby polynucleotide structure. The second and third single setups, 154 and 178, may be aligned in such a manner that when a portion of the polynucleotide structure extends beyond the second nanochannel 168, the first end region of the polynucleotide structure may be sensed by the fifth electrode 182 of the third single setup 178. Upon the fifth electrode 182 of the third single setup 178 senses the first end region of the polynucleotide structure, the fifth electrode 182 may be activated (i.e. ON) to generate a third electrostatic force, and at the same time, the fourth electrode 170 of the second single setup 154 may be deactivated (i.e. OFF). The deactivation of the second electrode 170 may cause the fourth electrode 170 to release the second end region of the polynucleotide structure. At this time, the fifth electrode 182 may apply the third electrostatic force to the first end region of the polynucleotide structure to pin the first end region of the polynucleotide structure near a surface thereof. On the other hand, the remaining part of the polynucleotide structure may be guided into the third nanochannel 180 under the influence of an electric force (e.g. a third electric force) applied along an axial direction of the third nanochannel 180 by the first and second electrodes 151 and 152 of the system 150 for sensing or sequencing purposes. The axial direction of the third nanochannel 180 may be aligned with the axial direction of the system 150.

As described above, depending on factors such as the size or complexity of the polynucleotide structure, more than two single setups may be required to unfold a polynucleotide structure in the pre-sensing stage of the system. In any event, the system illustrated in FIGS. 7A, 7B and 7C may perform a multi-stage polynucleotide stretching process to obtain a fully extended polynucleotide for sensing or sequencing purposes. Each single setup may include a nanochannel and an electrode positioned adjacent to an inlet of the nanochannel. Each single setup may be aligned in such a manner that the polynucleotide structure can be subject to a consistent unfolding process. When an electrode of a single setup detects the presence of the polynucleotide structure, that electrode may be activated to generate an electrostatic force to pin the polynucleotide structure near the surface thereof, and simultaneously, the previous electrode may be deactivated.

The length of each nanochannel is configured such that a portion of the polynucleotide structure in a fully extended form extends beyond the outlet of the nanochannel. In some embodiments, the length of each nanochannel in the system is half of the length of a fully extended polynucleotide. Each nanochannel may include a tapered inlet with a taper angle less than 45 degree. The width of each electrode positioned adjacent to an inlet of each nanochannel may be 100 nm.

In some embodiments, if the polynucleotide structure enters a nanochannel in a folded form, the system may detect such a situation based on noisy signals gathered from the nanochannel. To solve the problem, the system may invert the electric force (e.g. an electric field) applied along the axial direction of the nanochannel to reset the polynucleotide structure and restart the unfolding process.

In some other embodiments, the electric force applied along the axial direction of the nanochannel of a single setup may be created by a cyclic electric field. Using the cyclic electric field may also allow the electrode positioned adjacent to the inlet of the nanochannel to properly pin an end region of the polynucleotide structure near a surface thereof.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the present disclosure that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to cost, strength, durability, life cycle cost, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A system for stretching a polynucleotide structure, the system comprising:
    a nanochannel having an inlet, an outlet, a first end region, and a second end region;
    a first electrode positioned adjacent to the first end region of the nanochannel, the first electrode being positively charged;
    a second electrode positioned adjacent to the second end region of the nanochannel, the second electrode being negatively charged, the first and second electrodes being configured to generate an electric force along an axial direction of the nanochannel to guide the polynucleotide structure into the nanochannel to stretch the polynucleotide structure along the axial direction of the nanochannel; and
    a third electrode positioned adjacent to the inlet of the nanochannel and configured to generate an electrostatic force perpendicular to a surface of the third electrode and to apply the electrostatic force to the polynucleotide structure to pin an end region of the polynucleotide structure near the surface of the third electrode.

2. The system of claim 1, wherein the polynucleotide structure is a DNA structure, an RNA structure, or a PNA structure.

3. The system of claim 1, wherein the surface of the third electrode is charged with positive charges.

4. The system of claim 1, wherein the electric force is an electric field.

5. The system of claim 1, wherein a width of the third electrode is 100 nm.

6. The system of claim 1, wherein a length of the nanochannel is configured such that a portion of the polynucleotide structure in a fully extended form extends beyond the outlet of the nanochannel.

7. The system of claim 1, wherein the inlet has a taper angle less than 45 degree.

8. A multi-stage system for stretching a polynucleotide structure, the multi-stage system comprising:
    a first nanochannel having a first inlet, a first outlet, a first end region, and a second end region;
    a first electrode positioned adjacent the first end region of the nanochannel, the first end region of the nanochannel being a first end region of the multi-stage system, the first electrode being positively charged;
    a second electrode positioned adjacent the second end region of the nanochannel, the second end region of the nanochannel being at a second end region of the multi-stage system, the second electrode being negatively charged, the first and second electrode being aligned axially;
    a third electrode positioned adjacent to the first inlet of the first nanochannel and configured to sense a presence of the polynucleotide structure and to generate a first electrostatic force perpendicular to a surface of the third electrode and to apply the first electrostatic force to the polynucleotide structure to pin a first end region of the polynucleotide structure near the surface of the third electrode, the first and second electrodes being configured to generate a first electric force along an axial direction of the nanochannel to guide the polynucleotide structure into the first nanochannel to stretch the polynucleotide structure along the axial direction of the nanochannel;
    a second nanochannel having a second inlet and a second outlet, the second nanochannel being positioned adjacent to the first outlet of the first nanochannel; and
    a fourth electrode positioned adjacent to the second inlet of the second nanochannel and between the first and the second nanochannel, the fourth electrode being configured to sense the presence of a second end region of the polynucleotide structure when a portion of the polynucleotide structure extends beyond the first outlet of the first nanochannel and to generate a second electrostatic force perpendicular to a surface of the third electrode, the fourth electrode being activated upon sensing the presence of the second end region of the polynucleotide structure and the third electrode being deactivated to release the first end region of the polynucleotide structure, the fourth electrode being configured to apply the second electrostatic force to the polynucleotide structure to pin the second end region of the polynucleotide structure near the surface of the fourth electrode, the first and second electrodes being configured to generate a second electric force to guide the polynucleotide structure through the second nanochannel.

9. The multi-stage system of claim 8, further comprising:
    a third nanochannel having a third inlet and a third outlet, the third nanochannel being positioned adjacent to the second outlet of the second nanochannel; and
    a fifth electrode positioned adjacent to the third inlet of the third nanochannel and between the second and the third nanochannel, the fifth electrode being configured to sense a presence of the first end region of the polynucleotide structure when a portion of the polynucleotide structure extends beyond the second outlet of the second nanochannel and to generate a third electrostatic force perpendicular to a surface of the fifth electrode, the fifth electrode being activated upon sensing the presence of the first end region of the polynucleotide structure and the third electrode being deactivated to release the second end region of the polynucleotide structure, the fifth electrode being configured to apply the third electrostatic force to the polynucleotide structure to pin the first end region of the polynucleotide structure near the surface of the fifth electrode, the first and second electrodes being configured to generate a third electric force to guide the polynucleotide structure through the third nanochannel.

10. The multi-stage system of claim 9, wherein the polynucleotide structure is a DNA structure, an RNA structure, or a PNA structure.

11. The multi-stage system of claim 9, wherein a width of each of the third, fourth, and fifth electrode is 100 nm.

12. The multi-stage system of claim 9, wherein a length of each of the first, second, and third nanochannels is configured such that a portion of the polynucleotide structure in a fully extended form extends beyond each of the first, second and third nanochannels.

13. The multi-stage system of claim 9, wherein the first, second, or third inlet is tapered.

14. The multi-stage system of claim 13, wherein the first, second, or third inlet has a taper angle less than 45 degree.

15. A system for stretching a polynucleotide structure, the system comprising:
a nanochannel having an inlet, an outlet, a first end region, and a second end region, the inlet of the nanochannel is tapered;
a first electrode positioned adjacent to the first end region of the nanochannel, the first electrode being positively charged;
a second electrode positioned adjacent to the second end region of the nanochannel, the second electrode being negatively charged, the first and second electrodes being configured to generate an electric force along an axial direction of the nanochannel to guide the polynucleotide structure into the nanochannel to stretch the polynucleotide structure along the axial direction of the nanochannel; and
a third electrode positioned adjacent to the inlet of the nanochannel and configured to generate an electrostatic force perpendicular to a surface of the third electrode and to apply the electrostatic force to the polynucleotide structure to pin an end region of the polynucleotide structure near the surface of the third electrode.

16. The system of claim 15, wherein the polynucleotide structure is a DNA structure, an RNA structure, or a PNA structure.

17. The system of claim 15, wherein the surface of the third electrode is charged with positive charges.

18. The system of claim 15, wherein the electric force is an electric field.

19. The system of claim 15, wherein a width of the third electrode is 100 nm.

20. The system of claim 15, wherein a length of the nanochannel is configured such that a portion of the polynucleotide structure in a fully extended form extends beyond the outlet of the nanochannel.

* * * * *

UNITED STATES PATENT AND TRADEMARK OFFICE
CERTIFICATE OF CORRECTION

| | | |
|---|---|---|
| PATENT NO. | : 11,872,561 B2 | Page 1 of 1 |
| APPLICATION NO. | : 17/200038 | |
| DATED | : January 16, 2024 | |
| INVENTOR(S) | : Karim Gadelrab et al. | |

It is certified that error appears in the above-identified patent and that said Letters Patent is hereby corrected as shown below:

In the Claims

Column 14, Line 7, Claim 7:
After "The system of claim"
Delete "1"
Insert --15--.

Signed and Sealed this
Thirty-first Day of December, 2024

Derrick Brent
*Acting Director of the United States Patent and Trademark Office*